(12) United States Patent
Fatemi (10) Patent No.: US 9,717,471 B2
(45) Date of Patent: Aug. 1, 2017

(54) METHOD AND APPARATUS FOR MULTIPLE-WAVE DOPPLER VELOCITY METER

(75) Inventor: Mostafa Fatemi, Rochester, MN (US)

(73) Assignee: MAYO FOUNDTION FOR MEDICAL EDUCATION AND RESEARCH, Rochester, MN (US)

( * ) Notice: Subject to any disclaimer, the term of this patent is extended or adjusted under 35 U.S.C. 154(b) by 1101 days.

(21) Appl. No.: 13/296,438

(22) Filed: Nov. 15, 2011

(65) Prior Publication Data

US 2012/0130248 A1 May 24, 2012

Related U.S. Application Data

(60) Provisional application No. 61/416,657, filed on Nov. 23, 2010.

(51) Int. Cl.
*A61B 5/05* (2006.01)
*A61B 8/06* (2006.01)

(52) U.S. Cl.
CPC ...................... *A61B 8/06* (2013.01)

(58) Field of Classification Search
USPC ....................... 600/407, 437, 441
See application file for complete search history.

(56) References Cited

U.S. PATENT DOCUMENTS

| | | | |
|---|---|---|---|
| 3,510,833 A | 5/1970 | Turner | |
| 4,255,977 A | 3/1981 | Newhouse et al. | |
| 4,296,482 A | 10/1981 | Kritz | |
| 5,903,516 A * | 5/1999 | Greenleaf et al. | ............... 367/92 |
| 2009/0292208 A1 * | 11/2009 | Jeffrey et al. | ................. 600/454 |

OTHER PUBLICATIONS

"Low-cost Vector Doppler System Utilizing Diffraction-Grating Transducers" by D. Vilkomerson et al. IEEE Ultrasonic Symposium. pp. 1491-1496. 2000.*
Zheng, Yi., et al.: Kalman Filter Motion Detection for Vibroacoustography using Pulse Echo Ultrasound, 2003 IEEE Ultrasonics Symposium, 1812-1815.
Ricci, Stefano et al.: A Dual Transducer Ultrasound System for Quantitative Doppler Measurements, IEEE 2007, 2718-2723.
Newhouse, V.L., et al.: Study of Vector Flow Estimation With Transverse Doppler, 1991 IEEE Ultrasonics Symposium, 1259-1263.
Gessner, Ryan et al.: High-resolution, high-contrast ultrasound imaging using a prototype dual-frequency transducer, 2009 IEEE International Ultrasonics Symposium Proceedings, 275-278.

(Continued)

*Primary Examiner* — Tse Chen
*Assistant Examiner* — Jason Ip
(74) *Attorney, Agent, or Firm* — Yakov Sidorin; Quarles & Brady LLP (57) ABSTRACT

A method and system for determining a velocity of a moving object such as a body or a stream. The object is irradiated in a non-collinear configuration with multiple ultrasound waves overlapping in a region-of-interest (ROI) of the object. An response wave, resulting from the non-linear interaction among the incident waves and the object, is detected and the frequency variations of the response wave are determined. Data representing a Doppler-shift of this frequency is further determined and processed to calculate the velocity of the moving object.

10 Claims, 9 Drawing Sheets

(56) References Cited

OTHER PUBLICATIONS

McArdle, Andrew et al.: Demonstration of Three-Dimensional Vector Flow Estimation Using Bandwidth and Two Transducers on a Flow Phantom, Pergamon—Ultrasound in Med. & Bio., vol. 21, No. 5, pp. 679-692, 1995.
Fatemi, Mostafa et al.: Ultrasound-Stimulated Vibro-Acoustic Spectrography, Science * vol. 280 * Apr. 3, 1998 * www.sciencemag.org, pp. 82-85.
Fatemi, Mostafa et al.: Vibro-acoustography: An imaging modality based on ultrasound-stimulated acoustic emission, Proc. Natl. Acad. Sci. USA, vol. 96, pp. 6603-6608, Jun. 1999.

\* cited by examiner

METHOD AND APPARATUS FOR MULTIPLE-WAVE DOPPLER VELOCITY METER

CROSS-REFERENCE TO RELATED APPLICATIONS

This application claims the benefit of and priority from a U.S. Provisional Patent Application No. 61/416,657 filed on Nov. 23, 2010 and titled "METHOD AND APPARATUS FOR MULTIPLE-WAVE DOPPLER VELOCITY METER." The disclosure of the above-mentioned patent application is incorporated herein by reference in its entirety.

TECHNICAL FIELD

The present invention relates to systems and methods for Doppler-based tracking to measure the motion of an object. In particular, the invention relates to using of multiple wave-emitting sources and resulting wave(s) produced by the non-linear interaction of the waves emitted by such sources for the determination of the object's velocity based on the measurement of a shift in frequency of the resulting wave.

BACKGROUND

Doppler techniques generally rely on a direct determination of the frequency shift of the primary wave caused by reflection of the wave off of the object upon which it impinges. Depending on the application, the Doppler system may utilize various sources of radiation such as, for example, acoustic, ultrasound (US), or electromagnetic. In imaging applications, for example, a Doppler system may be incorporated in a real-time scanning imaging system, such as an US imaging system.

Ultrasonic Imaging.

Various ways are known in which ultrasound can be used to produce images of objects. In the so-called "transmission mode", for example, an ultrasound transmitter may be placed on one side of an object so as to have sound transmitted through the object to the ultrasound receiver that is placed on the other side of the object. With transmission mode methods, an image may be produced in which brightness of each pixel of an image is a function of the amplitude of the ultrasound wave that reaches the receiver ("attenuation" mode), or in which the brightness of each pixel of the displayed image is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver (this is referred to as "refraction", "backscatter" or "echo" mode).

Several backscatter methods for acquiring ultrasound data are known. In the so-called "A-scan" method, an ultrasound pulse is directed into the object by the transducer and the amplitude of the reflected sound is recorded over a period of time. The amplitude of a response signal (also referred to as an echo signal) is proportional to the scattering strength of reflecting elements in the object and the time delay is proportional to a distance separating these reflectors from the transducer. In the so-called "B-scan" method, the transducer transmits a series of ultrasonic pulses as it is scanned across the object along a single axis of motion. The resulting response signals are recorded in a fashion similar to that of the A-scan method, and the amplitudes of these response are used to modulate the brightness of pixels on a display. The location of the transducer and the time delay values of the received response signals determine which display pixels are to be illuminated. With the B-scan method, enough data are acquired from which a two-dimensional (2D) image of the reflecting elements can be reconstructed. Rather than physically moving the transducer over the subject to perform a scan, sometimes an array of transducer elements is employed while an ultrasonic beam is electronically moved or scanned over a region of interest.

Ultrasonic transducers for medical applications are known to include one or more piezoelectric elements sandwiched between a pair of electrodes. A typical piezoelectric element is constructed of lead zirconate titanate (PZT), polyvinylidene diflouride (PVDF), or PZT ceramic/polymer composite. The electrodes of the piezo-element are connected to a voltage source, and application of voltage to the piezo-element triggers its change of dimensions at a frequency corresponding to that of the applied voltage. When a voltage pulse is applied, the piezoelectric element emits an ultrasonic wave, into the media to which it is coupled, at frequencies present in the excitation pulse. Conversely, when an ultrasonic wave strikes the piezoelectric element, the element produces a corresponding voltage across its electrodes. Typically, the front of the element is covered with an acoustic matching layer that improves acoustical coupling with the media in which the ultrasonic waves propagate. In addition, a backing material may be disposed to the rear of the piezoelectric element to absorb ultrasonic waves that emerge from the back side of the element so that they do not interfere. A number of such ultrasonic transducer constructions have been disclosed (see, for example, U.S. Pat. Nos. 4,217,684; 4,425,525; 4,441,503; 4,470,305 and 4,569,231).

When used for ultrasound imaging, the transducer typically has a number of piezoelectric elements arranged in an array and driven with separate voltages (apodizing). By controlling the time delay (or phase) and amplitude of the applied voltages, the ultrasonic waves generated, in the transmission mode, by such a phase array of piezoelectric elements combine to produce a net ultrasonic wave focused at a selected point. By controlling the time delay and amplitude of the applied voltages, this focal point can be moved in a plane to scan the subject.

The same principles apply when the transducer is employed to receive the reflected sound (in the receiving mode). Specifically, the voltages produced at the transducer elements in a phase-array are summed together such that the net signal is indicative of the sound reflected from a single focal point in the subject. As with the transmission mode, this focused reception of the ultrasonic energy is achieved by imparting separate time delay (and/or phase shifts) and gains to the response signal received by each transducer array element.

US Doppler System.

The ultrasound (US) investigation represents a non-invasive, diffuse, and low-cost method capable of evaluating the blood velocity by exploiting the Doppler effect. The US Doppler systems employ an ultrasonic beam to measure the velocity of moving reflectors, such as flowing blood cells. The blood velocity is detected by measuring the Doppler shifts in frequency imparted to ultrasound by reflection from moving red blood cells. Accuracy in detecting the Doppler shift at a particular point in the bloodstream depends on defining a small sample volume at the required location and then processing the responses to extract the Doppler shifted frequencies. The possibility of accurately measuring the velocity of an object or the flow of liquid such as, for example, the velocity of blood flowing in human blood-vessels represents a significant opportunity for hemodynamic research and early diagnosis of cardiovascular diseases.

The real-time scanning US system provides electronic steering and focusing of a single acoustic beam and enables small volumes to be illuminated anywhere in the field of view of the instrument, and to visually identify their locations on a two-dimensional B-scan image. A Fourier transform processor faithfully computes the Doppler spectrum backscattered from the sampled volumes, and by averaging the spectral components the mean frequency shift can be obtained. Typically the calculated blood velocity is used to color code pixels in the B-scan image.

The velocity information is obtained through processing the characteristics of the Doppler-shifted US-beam. According to the Doppler effect, an object moving with velocity v and impinged upon by a planar US-wave of frequency $f_0$ generates a response characterized by an angle-dependent frequency shift:

$$f_s = f_0 v \cos \phi / c \qquad \text{(Eq. 1);}$$

where $\phi$ is the Doppler angle defined between the object velocity vector and the k-vector of the wave incident upon the moving object, and c is the speed of a wave propagation in corresponding medium. One recognized limitation of this technique is that, by measuring the frequency $f_s$, only the axial component $v \cos \phi$ of the velocity can be estimated, and the knowledge of the Doppler angle $\phi$ is required to proceed with the quantitative measurement of v.

The described limitation led to a development of new techniques for estimating the velocity components along all of the spatial axes, such as techniques using dual transmitters, multiple lines of sights, multiple receivers, multi-plane detection, and speckle tracking. In most commercial US systems the problem is partially overcome by rough assessment of the Doppler angle with the help of a B-mode image and the use of the M-line and the reference line. In another example, in order to resolve the Doppler angle ambiguity, the related art proposed an approach involving the use of dual transmitters. This approach takes advantage of employing two Doppler sources such as US transducers, one of which is oriented transversely to the investigated vessel; of sensitivity of the resulting measurement to small deviations from the ideal 90° orientation of one of the Doppler sources; and of the fact that the resulting Doppler spectra are substantially symmetrical around the zero mean frequency.

A skilled artisan should recognize that currently-existing Doppler methods of measuring the velocity of a moving object endure specific shortcomings affecting either the precision of the resulting measurement, depending on a specific application, or the complexity of electronics used to carry out such measurements. For example, methods of the related art are based on the measurement of a Doppler-shift of a very high US frequency (i.e. a determination of a rather small value relative to the US frequency itself). This conventionally requires the use of a frequency demodulator and restrains the range of measurements to those of relatively high-speed objects. The use of Doppler technique in cardiovascular applications has an additional limitation imposed by insufficient spatial resolution of the Doppler technique. In particular, while the measurements of the superficial blood vessels of the body can be performed with a Doppler system operating in a continuous regime, the measurements of deep-lying blood vessels of the body often dictate that the Doppler system be operated in a pulsed regime, without which a satisfactory spatial resolution cannot be achieved. A pulsed Doppler system, however, is afflicted with a range-velocity product maximum that makes it substantially impossible for the system to measure the fastest blood flows occurring deep in the heart. The pulsed Doppler system may additionally have lowered signal-to-noise ratio. Finally, most of the Doppler systems employ transducers with such radiation patterns that limit the spatial resolution achievable during the measurement of the moving object.

Therefore, it would be desirable to have a system and method that is capable of determining the velocity of a moving object using US without being limited by the drawbacks of the prior-art.

SUMMARY OF THE INVENTION

The present invention overcomes these fundamental limitations of Doppler-based tracking methods by employing multiple sources of emitted waves and determining the velocity of the moving object by calculating the Doppler frequency shift in a wave that is produced non-linearly by the multiple emitted waves. For example, the Doppler frequency shift can be measured in a wave arising from the non-linear interaction of the multiple source waves and the moving object (such as a moving medium, for example), or that associates with non-linearity of the radiation force mechanism or nonlinear responsive behavior of the material. By way of example, the multiple sources of emitted waves may be ultrasound sources.

According to embodiments of the invention, a method is provided for characterizing motion in a region-of-interest (ROI) of an object, such as a biological tissue, with the use a Doppler system. In a specific embodiment, the motion is represented by the velocity. The method includes arranging multiple sources of waves (which may be sound waves, or waves in a chosen region of the electromagnetic, EM, spectrum) such that the sources generate at least two waves having generally different frequencies that non-collinearly impinge upon the ROI where they overlap. In one embodiment, the sources may be oriented such that at least two waves impinge upon the ROI at equal angles. The multiple waves impinging upon the object may have approximately equal frequencies.

The irradiation of the object with multiple waves includes converging or focusing the waves such that the waves overlap within their respective focal ranges. The method further includes producing interference of the first and second waves at the ROI and generating a response wave at a response frequency, the response wave being produced by a non-linear interaction of the at least two impinging waves and having several frequency components (such as a low-range frequency component, a mid-range frequency component, and a high-range frequency component) each of which is dependent on the motion in the ROI. In a specific embodiment, the response wave may be an acoustic wave and some of the components of the response wave (for example, at least one of the low- and the mid-range frequency components) may be audible and detectable through hearing, or have frequencies in a range adjoining the audible range and detectable with an acoustic detector such as a microphone or a hydrophone, while the high-range frequency component may have an ultrasound frequency.

In addition, the method may include detecting at least some of the components of the response wave (for example, the mid-range frequency component) and determining a value of a corresponding response frequency (for example, a mid-range frequency). In a specific embodiment, the determination of a component frequency of the response wave is carried out without employing the frequency demodulation.

Further, the method may include calculating a dynamic parameter (for example, velocity) that characterizes the motion in the ROI. Such calculation of the dynamic parameter may be based at least on the non-collinear geometry, the determined response frequency, and the frequencies of the waves impinging on the object.

Embodiments of the invention also provide a Doppler system including multiple sources of the emitted waves, configured to non-collinearly transmit respectively corresponding multiple waves that spatially overlap at an ROI of the object being tested such as a biological tissue, a fluid, a gas, or a solid body. The system additionally contains a receiver configured to detect a response wave produced in the ROI in response to a non-linear interaction between the multiple emitted waves and the object and to produce an output representing the detected response wave. The system also includes an electronic circuitry operably connected to the transmitter and receiver to accept an input data, representing and characterizing the transmission of the multiple waves and the receiver's output, and adapted to derive from these input data a dynamic characteristic of the ROI. The dynamic characteristic may include a velocity in the ROI and/or the object. In one embodiment, the multiple sources may be US transducers generating the US waves and detecting corresponding response waves while the electronic circuitry is devoid of a frequency demodulator. The electronic circuitry includes at least one of a frequency demodulator, an acoustic sensor, and a light detector, but in a specific embodiment may be devoid of the frequency demodulator. The object includes at least one of a biological tissue, a fluid, a gas, or a solid body.

Embodiments of the invention additionally contemplate a computer program product for use on a computer system for characterizing a motion in an ROI of the object being tested. The computer program product includes a computer usable medium having a computer readable program code thereon, the computer readable program code including program code for implementing the steps of the method of the invention.

BRIEF DESCRIPTION OF THE DRAWINGS

The foregoing and other advantages of the invention will appear from the following description. In this description, references are made to the accompanying drawings which form a part hereof, and in which there is shown, by way of illustration, a preferred embodiment of the invention. Such embodiment does not necessarily represent the full scope of the invention, however, and reference is made therefore to the claims for interpreting the scope of the invention. In the drawings:

DETAILED DESCRIPTION OF THE SPECIFIC EMBODIMENTS

As will be described, the present invention is applicable for use with a wide variety of wave sources and emitted waves. By way of example, the following description will make reference to acoustic systems such as ultrasound (US) systems and acoustic waves such as US waves. It is noted, however, that these are but specific examples of wave sources and emitted waves. Other examples may include sound waves outside of the US range, or electromagnetic waves such as light or microwaves.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described features, structures, or characteristics of the invention may be combined in any suitable manner in one or more embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

Figure 1:
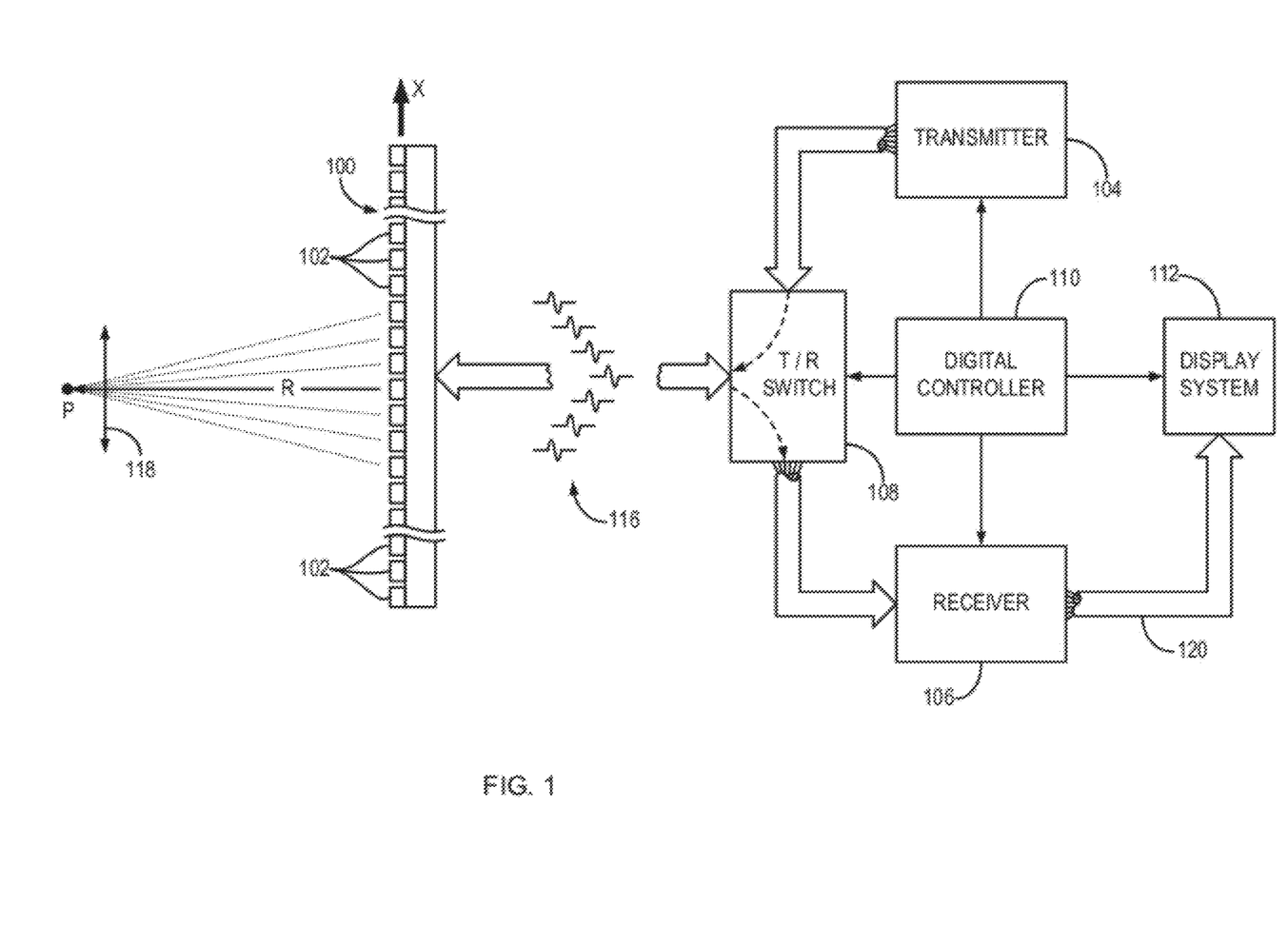
FIG. 1 is a block diagram of an exemplary ultrasonic imaging system configured to employ an embodiment of the present invention.

Referring to FIG. 1, an exemplary US system includes a transducer array 100 comprised of a plurality of separately driven elements 102, each of which produces a burst of ultrasonic energy when energized by a pulse generated by a transmitter 104. The ultrasonic energy reflected back to the transducer array 100 from the subject under study (SUT, not shown) is converted to an electrical signal by each transducer element 102 and applied separately to a receiver 106 through a set of switches 108. The transmitter 104, receiver 106, and the switches 108 are operated under the control of a digital controller 110 responsive to the commands input by a human operator. A complete scan is performed by acquiring a series of responses in which the switches 108 are set to their "transmit" position, the transmitter 104 is gated "on" momentarily to energize each transducer element 102, the switches 108 are then set to their "receive" position, and the subsequent response signals produced by each transducer element 102 are applied to the receiver 106. The separate response signals from each transducer element 102 are combined in the receiver 106 to produce a single "response" signal that is further employed to produce a line in an image displayed on a display system 112.

The transmitter 104 may drive the transducer array 100 in such a fashion as to direct the produced ultrasonic beam substantially perpendicular to a front surface of the array 100. Referring particularly to FIG. 1, to focus this beam at a range R from the transducer array 100, a subgroup of the elements 102 are energized to produce the beam and the pulsing of the elements 102 that are located in a central portion of the array 100 in this subgroup are delayed relative to those elements 102 that are located in a peripheral portion of the array 100. Consequently, as a result of the interference of the small separate wavelets produced by the subgroup elements, a generated acoustic beam is focused at a point P. The time delay values associated with pulsing of the element 102 determine the depth of focus, or range R, which can be changed during a scan; the purpose of which is to produce a two-dimensional image. The same time delay pattern is used when receiving the response signals resulting in dynamic focusing of the response signals received by the subgroup of elements 102. In this manner a single scan line in the image is formed.

To generate the next scan line, the sub-group elements to be energized is shifted by one element-position along the transducer length and another scan line is acquired in a fashion similar to that described above. In operation, therefore, the focal point P of the ultrasonic beam is thus shifted (not shown) along the length of the transducer 100 by repeatedly shifting the location of the energized subgroup of elements 102.

It would be appreciated that, alternatively or in addition, the transducer 100 may be driven to produce an ultrasound beam that is scanned or steered angularly.

Recognition of the motion of an object on a local scale with the use of Doppler US imaging in any number of scans (alternately referred to as "image frames") acquired in a given scan-line is based on correlation between the pulses, transmitted and reflected along the corresponding scan-lines (beams), and depth, or distance from the transducer element 102. A typical two-dimensional (2D) US image frame may consist of hundreds of scan-lines, and a train of US pulses is sent along each scan-line. As a result, formation of each Doppler-image frame requires numerous correlations of pulses to ultimately be displayed on the display system 112.

According to embodiments of the present invention, Doppler-based measurements of a dynamic characteristic of an object—which may be a single object within a region-of-interest (ROI) or an entire ROI within a larger object such as, in a specific example, a biological tissue—is carried out based on characterization of a complex, multi-frequency wave generated by such object in response to a non-linear propagation and/or interaction of multiple waves impinging upon the object. Detection of this responsive multi-frequency wave allows the user to determine frequencies of the detected wave and calculate the dynamic characteristic of the object (such as the object's velocity, for example) based at least in part on the responsive wave frequencies and the geometry of the wave propagation with respect to the direction of the object's motion.

A non-limiting illustration of the principle of operation of the invention is presented based on the example of US-waves used to detect the motion of a fluid such as blood. As shown in a schematic diagram of FIG. 2, sources 201 and 202 transmit continuous (or substantially-continuous) waves (CWs) 211, 212, at respective frequencies $f_1$ and $f_2$, towards a moving object 214. In the case illustrated by FIG. 2, the moving object 214 is fluid flowing with velocity v in a direction indicated by an arrow 220. Generally, the fluid may contain some particles such as blood cells. Although the waves 211, 212 are shown to be converging towards the object, it is understood that the use of non-converging wave (such as, for example, plane waves) does not change the principle of operation of the embodiments of the invention. The CWs 211, 212 can be constructed in a variety of ways. To generate the converging waves and, in particular, the spherical waves focused on and overlapping in the ROI, the US-sources 201, 202 can include the elements appropriately configured transducers (such as spherically-shaped piezo-electric caps or an array transducer) driven by two CW signals at corresponding frequencies. In one embodiment, the overlap of the converging waves in the ROI occurs in Rayleigh ranges respectively corresponding to the converging waves. In a related embodiment (not shown), the transducers 201, 202 are configured to generate plane US-waves.

Figure 2:
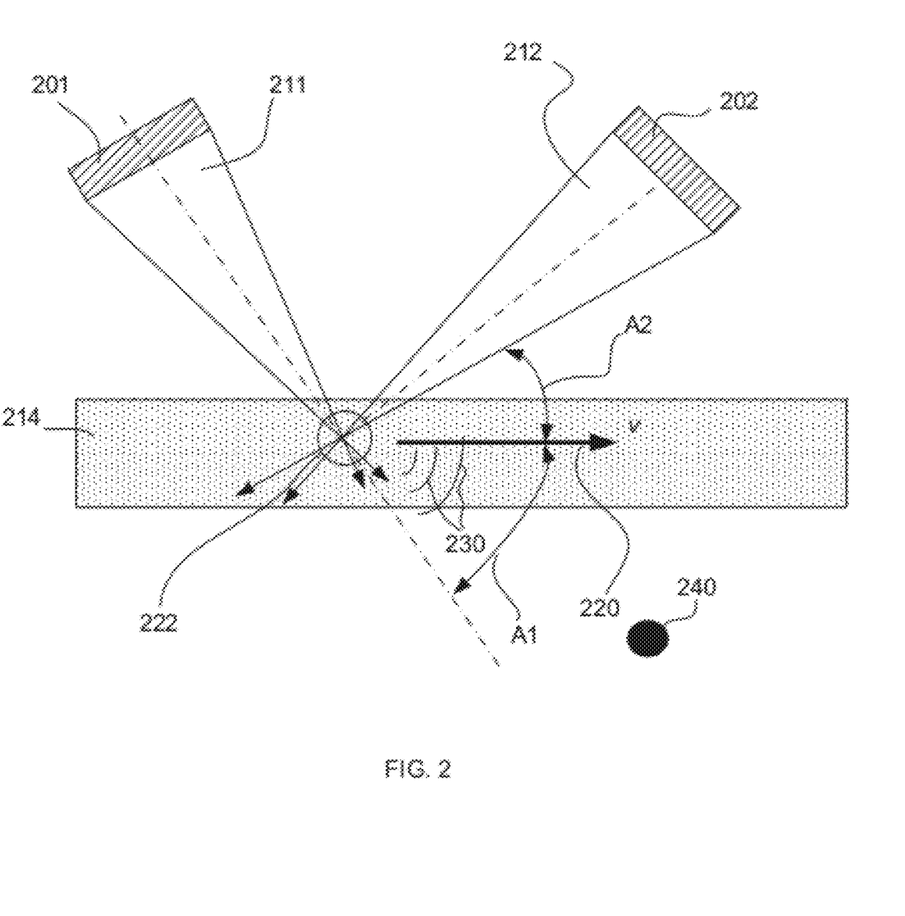
FIG. 2 is a schematic diagram illustrating non-collinear geometry of irradiation of a moving object with multiple ultrasound waves according to an embodiment of the invention.

In further reference to FIG. 2, the waves 211, 212 are impinging upon the object 214 in a non-collinear geometry so as to overlap or intersect each other in an ROI 222. The non-collinearity of the incident waves 211, 212 is indicated by angles of incidence $A_1$ and $A_2$. In a specific embodiment, the moving object 214 can be irradiated symmetrically, in that $A_1=A_2$.

According to the Doppler principle, the ROI 222 experiences the incident waves 211, 212 at frequencies:

$$f'_1 = f_1(1 - v \cos A_1/c) \qquad \text{(Eq. 2a), and}$$

$$f'_2 = f_2(1 + v \cos A_2/c) \qquad \text{(Eq. 2b).}$$

As the two waves 211, 212 interact with the object 214 within the localized area of overlap such as the ROI 222, the waves 211, 212 generate a radiation force that causes (according to principles of vibro-acoustography) the ROI 222 to vibrate and, thereby, generate a response wave. The principles of vibro-acoustography are described, for example, by Fatemi et al. (*Proc. Nat'l Acad. Sci. USA, Engineering*, v. 96, pp. 6603-6608, June 1999, pp. 6603-6608), which is incorporated herein by reference. The radiation force characterized by a frequency $f_3$ has low-range frequency and high-range frequency components, according to:

$$f_3 = f'_2 - f'_1 = f_A + v(f_2 \cos A_2 + f_1 \cos A_1)/c \qquad \text{(Eq. 3),}$$

where $f_A = f_2 - f_1$. Accordingly, the response wave 230, that is generated by and emanating from the moving ROI 212 in response to the incident waves 211, 212, is characterized by a frequency $f_3$ and has corresponding low-range frequency component and a high-range frequency component that are dependent on the velocity of the object motion. Detection of the response wave 230 with one of the detecting systems 240 known in the art allows the user to determine the frequency $f_3$ and the velocity of the object's motion from Eq. (3) based at least on the geometry of irradiation of the object 214 with the waves 211, 212 and the knowledge of the nature of the object defining the value of c. It is appreciated that the described embodiment allows for determination of both the speed and the direction of the object's motion because the sign of the frequency shifts in Eqs. (2a, b) depends on the direction of the motion of the object.

In a specific case, when the sources 201, 202 are configured to generate waves at frequencies $f_1 \approx f_2$ that are close enough to produce interference in the overlap region, the response wave 230 will have a low-range frequency component in a region of the frequency spectrum that is within or adjoins the audible range (for example, between zero and several tens of kHz). Such low-frequency wave can therefore be detected with a simple microphone or a hydrophone or even heard by a human. For example, the detection of a response wave 230 (non-linearly formed in response to interaction between the radiation force of an amplitude-modulated field that is created by the two US beams 211, 212 emitted at substantially equal frequencies and at substantially equal angles $A_1 \approx A_2$ with respect to the direction of the object's motion) can be carried out at an audible frequency f that represents an amount by which the moving object (for example, particles in the flow 214) shifts the frequency of irradiating waves due to the motion of the object. The detection can be implemented with such a detecting system 240 as, for example an audio receiver. In one embodiment, the receiver 240 may include a stethoscope transmitting the sound that has resulted from the detection of the response wave to the user's ears. In another embodiment, the receiver 240 may include a microphone optionally complemented with an amplifier and a headphone speaker. Such embodiment would allow the user to detect the object's motion simply by listening to the generated sound, and to estimate the speed of the motion by recognizing that the higher pitch of the generated sound corresponds to the higher speed of motion while the lower pitch corresponds to the lower speed of object motion.

Figure 3:
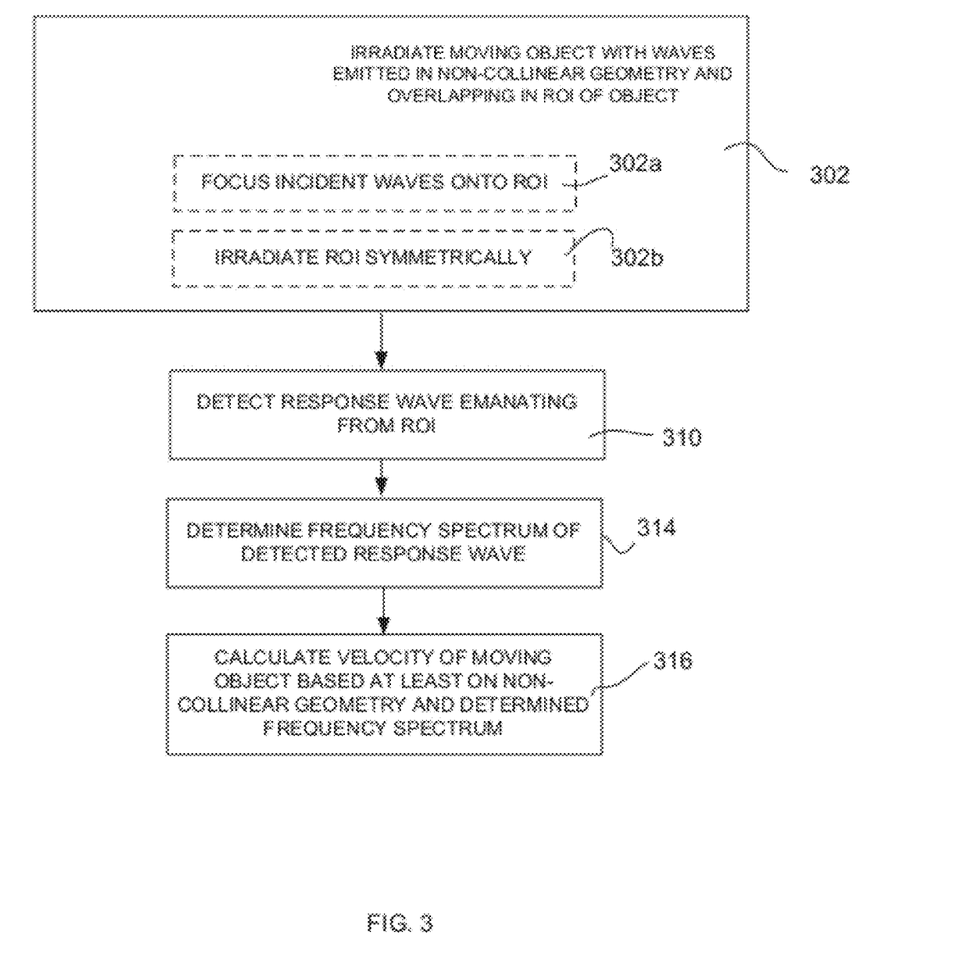
FIG. 3 is a flow-chart describing a process of determination of the object velocity with the use of an embodiment of FIG. 2.

Turning to FIG. 3, a flow chart is provided setting forth an example of an algorithm in accordance with an embodiment of the invention. At step 302, the moving object is non-collinearly irradiated with at least two waves (such as US waves, for example). At least one of the irradiating waves is either a converging wave, 302a, or a plane wave (not shown). In the specific embodiment of FIG. 3, both emitted waves irradiating the object are focused onto the ROI. The orientation of sources producing the irradiating is such that these irradiating waves overlap in the ROI of the object. Optionally, at step 302b, the non-collinear geometry of irradiation may be such as to assure that k-vectors of the irradiating waves lie in the same plane at equal but opposite-sign angles with respect to the direction of the object's motion. Following the irradiation of the ROI, a response wave generated by an irradiation-caused vibration within the ROI is detected, at step 310, to determine a frequency spectrum of the response wave at step 314. The determined frequency spectrum includes a difference frequency equal to the difference of frequencies of two irradiating waves. Based on the determined frequency spectrum and geometric parameters of irradiation scheme, both the speed and direction of motion of the object is then calculated at step 316.

Figure 7:
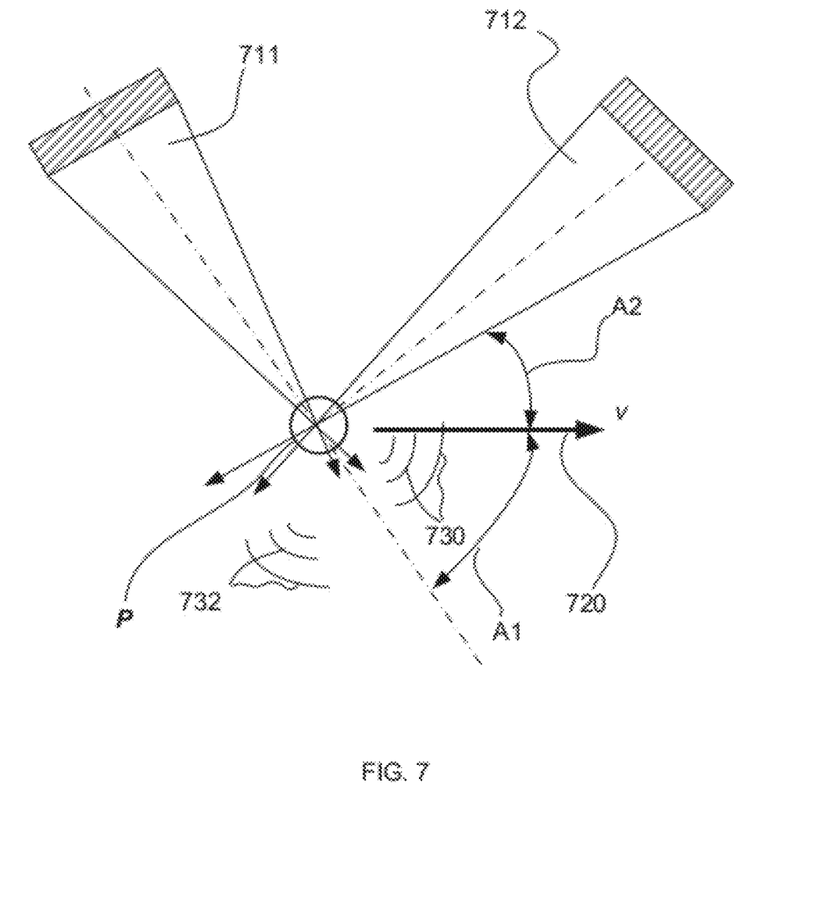
FIG. 7 is a schematic diagram showing generalized geometry of irradiation of a moving object according to an embodiment of the invention.

In reference to FIG. 7 and in further reference to FIG. 2, the embodiment of FIG. 2 is further generalized under the assumption that the angles of incidence of the two irradiating waves are equal, but opposite in sign. (A similar analysis can be performed by a skilled artisan for a general case of unequal angles of incidence.) Specifically, having been exposed to irradiating CWs 711, 712 having corresponding frequencies $f_1$ and $f_2$ and having perceived these irradiating waves as having frequencies:

$$f''_1 = f_1 - qf_1 \qquad \text{(Eq. 4a),}$$

and $$f''_2 = f_2 + qf_2 \qquad \text{(Eq. 4b),}$$

where $q = v \cos A/c$, an object P (the motion of which in medium characterized by c is defined by a vector 720, $\vec{v}$,) scatters the incident waves as waves 730, 732 having respective frequencies $f''_1$, $f''_2$. Due to the motion of the object P, frequencies of the scattered waves depend on the location of the observation point. The frequency-shift corresponding to each of the incident waves falls within the range from $-q$ to $+q$:

$$f'_1 = f_1 + K_1 q f_1 \quad \text{(Eq. 5a)},$$

$$f'_2 = f_2 + K_2 q f_2 \quad \text{(Eq. 5b)},$$

where $-1 \leq K_1, K_2 \leq +1$. Therefore, while the moving object P interacts with the waves at frequencies $f_1, f_2$, any stationary point in the surrounding medium interacts with a plurality of waves corresponding to frequencies $f_1, f_2, f''_1, f''_2$.

According to principles of vibro-acoustography, the radiation force produced by the plurality of waves at a chosen point in the medium penetrated with the plurality of waves is proportional to the square of the field generated at this stationary point. A secondary, response wave (generated by the moving object P due to vibration caused by the radiation force acting upon the object) includes high-frequency components and low-range frequency components at frequencies corresponding to summation and subtraction of the frequencies of the impinging waves as a result of non-linear interaction between the incident waves and the object.

The spectrum of the response wave contains at least the following components, for $-1 \leq K_1, K_2 \leq +1$:

$$f_{31} = f_d = f_2 - f_1$$

$$f_{32} = f''_2 - f_1 = f_d + q(1+K_2)f_2$$

$$f_{33} = f_2 - f''_1 = f_d + 1(1-K_1)f_1$$

$$f_{34} = f''_2 - f''_1 = f_d + q(f_1 + f_2) - q(K_2 f_2 - K_1 f_1)$$

$$f_{35} = f_1 - f''_1 = q(1-K_1)f_1 \quad \text{(Eq. 6)},$$

where $f_{31}$ does not depend on the object's motion; $f_{32}, f_{33}$, and $f_{34}$ represent corresponding mid-range frequency Doppler shifts from the difference frequency $f_{31} = f_d$; $f_{35}, f_{36}$ represent a very low-range frequency wave components. By way of example and assuming that the two impinging waves have very close frequencies, $f_1 \approx f_2 = f_0 = (f_1 + f_2)/2$, and assigning $f_v = 2qf_0$, the spectral components of the response-wave generated by the object in response to the two incident waves fall within the following ranges:

$$f_d \leq f_{32} \leq f_d + f_v$$

$$f_d \leq f_{33} \leq f_d + f_v$$

$$f_d \leq f_{34} \leq f_d + 2f_v$$

$$0 \leq f_{35} \leq f_v$$

$$0 \leq f_{36} \leq f_v \quad \text{(Eq. 7)}.$$

Figure 4:
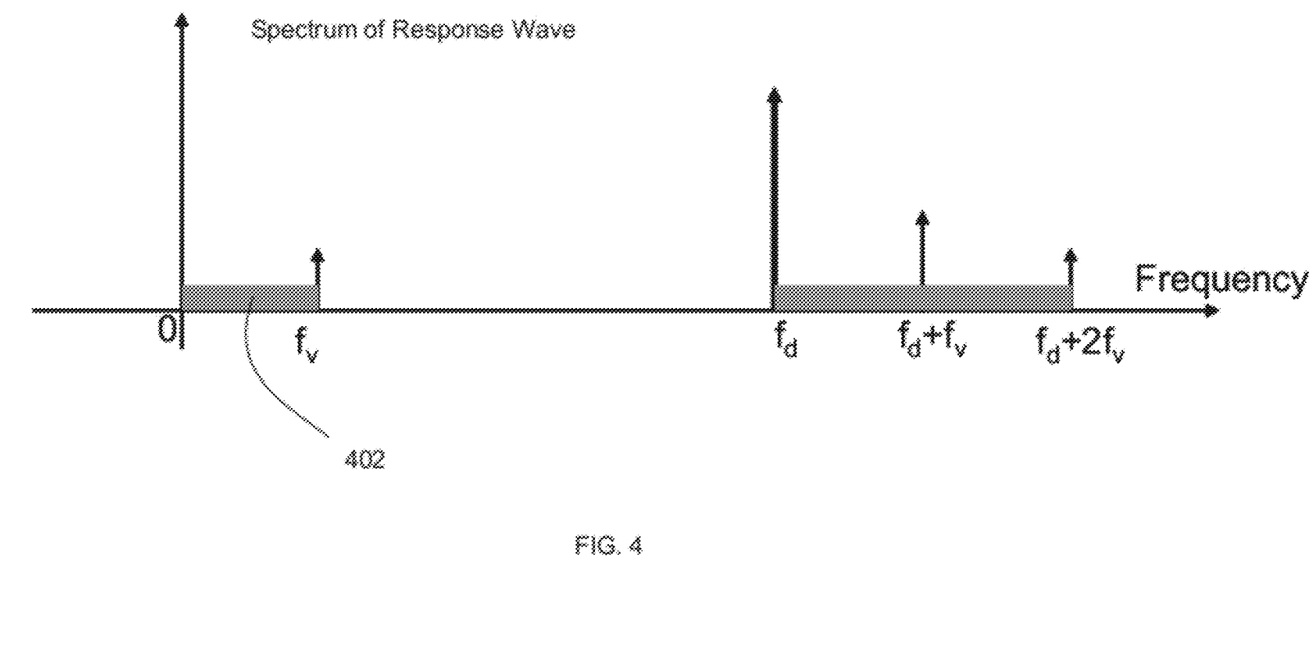
FIG. 4 is a schematic diagram depicting portions of the spectrum of a response wave formed as a result of non-linear interaction among the multiple incident waves and the moving object.

A frequency spectrum corresponding to such generalized response-wave is illustrated in FIG. 4. According to embodiments of the present invention, measurement of the motion of the object can be carried out by detecting the response waves within the spectral ranges illustrated in FIG. 4 followed by determining, based on such detection, the major frequency components present and calculating the value of v in accordance with Eqs. (4-7).

Determination of the object's velocity may also be carried out in several ways, including wave-detection at mid-range frequencies, low-range frequencies, and high-range frequencies. In one embodiment, for example, the object's velocity may be derived based on the detection of a response wave at at least one of the mid-range frequencies $f_{32}, f_{33}$, and $f_{34}$. In the alternative embodiment, it is possible to infer the value of $f_v$ by evaluating the range of frequencies present in the spectrum of the response-wave, that are higher than the difference frequency $f_d$. Once $f_v$ is determined, value of v is then defined with the use of:

$$v = f_v c/(2f_0 \cos A) \quad \text{(Eq. 8)}.$$

Figure 5A:
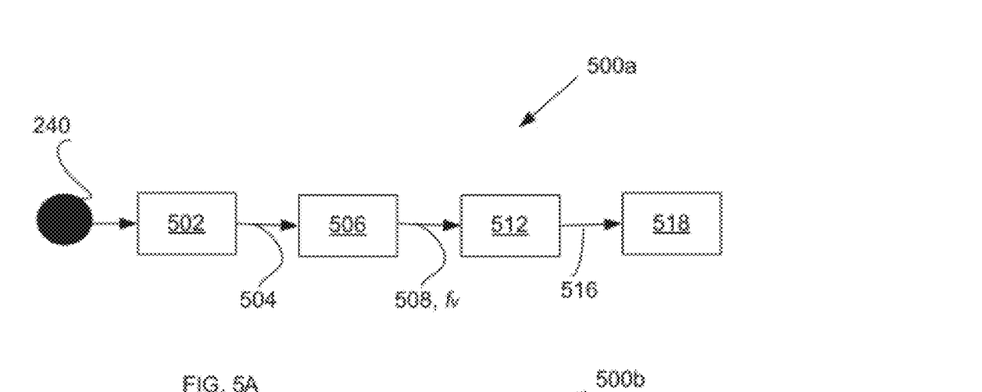
FIG. 5A is a schematic diagraph illustrating an embodiment of a system used for processing of the data representing the mid-range frequency components of a response wave detected with the use of the non-collinear geometry of FIG. 2.

It would be appreciated that embodiments of a system and a method of the present invention are advantageous in that they allow to assess v without the use of a demodulator, which is conventionally employed in Doppler US systems. In particular, according to an embodiment of the invention, a process of determining a frequency component of a response wave is devoid of frequency demodulation. As is schematically shown in FIG. 5A, measurement of $f_v$ can be carried out by a system 500a that directly filters the output signal of the detector (such as detector 240 of FIG. 2) with the use of a frequency filter 502 such as a band-pass filter, for example, to extract mid-range frequency components of the response wave. The embodiment of FIG. 5A further includes a frequency-measurement device 506 such as, for example, a spectrum analyzer, a Fourier transformer, a zero-crossing counter, or an electronic frequency-to-voltage converter that in-takes an output 504 of the filter 502 and delivers a value 508 of the determined $f_v$ to a processor 512. The processor 512, in turn, performs appropriate calculations to extract data 516 representing the motion of the object in the chosen coordinate system, which can be appropriately presented to the operator with the use of a display 518.

Figure 5B:
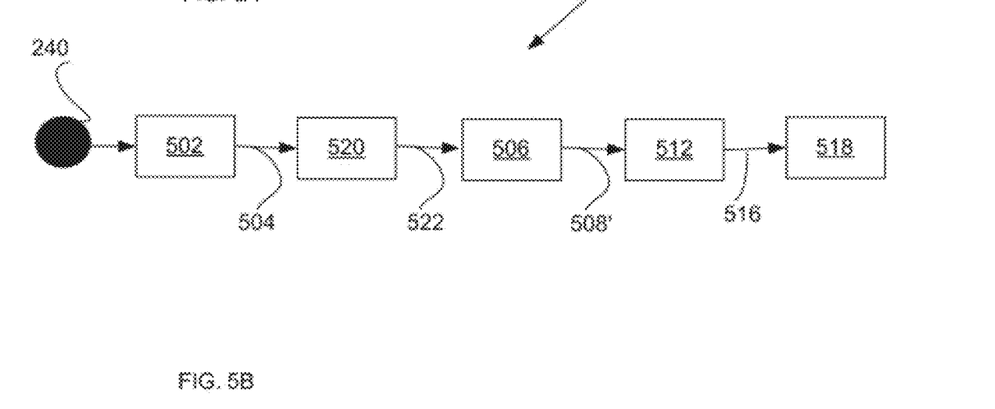
FIG. 5B is a schematic diagraph illustrating an embodiment of a system used for processing of the data representing the high-frequency components (such as US) of a response wave detected with the use of the non-collinear geometry of FIG. 2.

In an alternative embodiment 500b of FIG. 5B, the motion of the object can be determined with the use of a traditional demodulation technique, where the output 502 of the detector 540 is frequency-filtered with the filter 502 to extract wave-components having frequencies in a region around $f_A$. The output 504 of the filter 502 is demodulated in a demodulator unit 520 using a demodulation method known in related art (such as, for example, super-heterodyne amplitude demodulation, coherent quadrature detection, or envelope detection) to deliver the output frequency components 522 to the frequency-measurement device 506. In a specific case when the dominant frequency of the response-wave is the one at $f_d + f_v$, the output 508' of the demodulator 506 would be a component at $f_v$.

In another alternative embodiment of the invention and in further reference to FIG. 4, the determination of the object's motion is based on detection of low-range frequency components of the response-wave aggregated in a spectral region 402. In effectuating the low-range frequency detection according to such embodiment of the invention, the corresponding signals are measured by a direct method similar to that discussed in reference to FIG. 5A. The detection of both mid-range and low-range frequency components of the Doppler-shifted wave is systemically simpler than the conventional detection that requires frequency demodulation. Embodiments of the present invention, therefore, provide an advantage over the conventional methods and systems.

In addition to the spectral components of Eq. (6), the spectrum of the response wave generally includes very-high frequency components (corresponding to US frequencies) and their harmonics not shown in FIG. 3, such as components at frequencies $f_1, f_2$ and around $f_1 + f_2$. Moreover, the skilled artisan will understand that the response-wave spectrum further includes higher-order terms corresponding to the interactions of multiply-scattered components of waves, or the components corresponding to the Doppler shift of the f components, i=1 . . . 6, resulting from the object's motion. In related embodiments, measurements of the object's velocity can be based on measurements of these very-high frequency components in a conventional manner of measuring a frequency Doppler shift.

In the traditional Doppler methods the velocity of the object is determined from measuring the frequency shift of a primary wave incident upon and reflected by the object. For example, in a CW Doppler method the velocity is calculated by measuring the shift in the primary ultrasound frequency. In the present invention, on the other hand, the frequency shift $f_v$ of a difference wave having a difference frequency is measured. Since the frequency $f_d$ of a difference wave (caused by non-linear interaction of the two primary ultrasound waves) is much smaller than the primary ultrasound frequencies $f_1$, $f_2$, the relative shift in frequency $f_v/f_d$ is much larger that the frequency shift of a primary wave (such as $f_v/f_1$, for example) and therefore is easier to measure. As an example and considering the case of ultrasound Doppler, if the ultrasound frequency is 5 MHz and the Doppler shift is 1 kHz, in the traditional Doppler method one needs to measure a relative shift of 1/5000 in frequency. As an example, an assumption is made that the ultrasound frequencies are 5 MHz and 5.050 MHz, i.e., $f_d$=50 kHz. To measure the frequency shift one needs to measure the shift of 1 kHz in a 50 kHz signal, which is a relative shift of 1/50 in frequency and, ratio-wise, is two orders of magnitude times greater than that of the traditional Doppler method. The fact that the frequency shift to be detected is so much greater that that detected conventionally leads to a more accurate velocity measurement and simpler electronics compared to the conventional Doppler velocity measurement methods. This feature of the present invention also makes it possible to measure very slow motion of an object. Additionally, the electronic circuitry for measuring such large frequency shift is much simpler than what would be needed for traditional Doppler flow measurement.

Figure 8A:
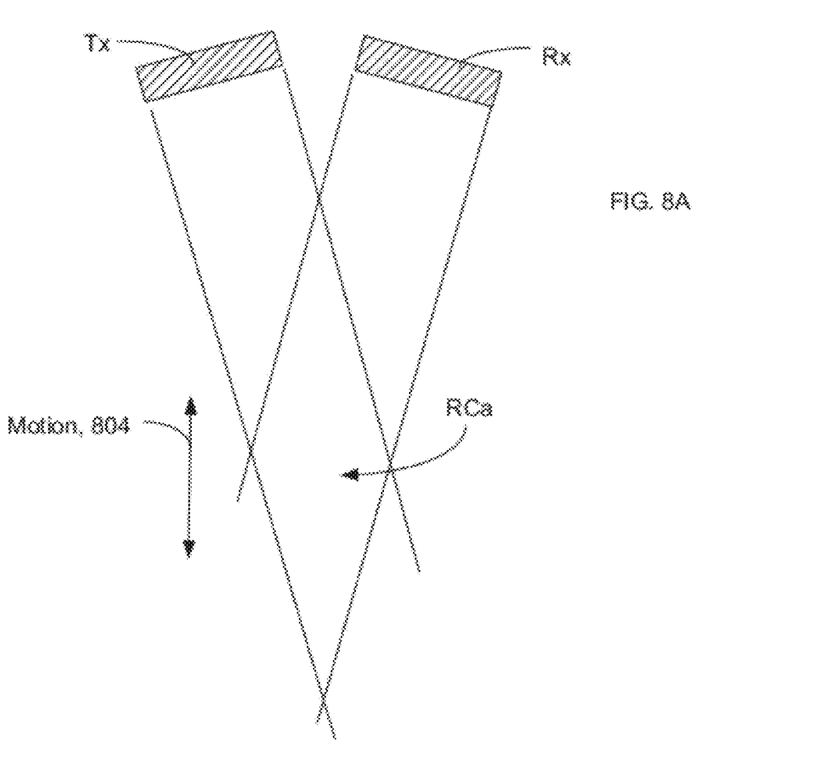
FIG. 8A is a diagram showing generalized geometry of a conventional CW Doppler having a large resolution cell.
Figure 8B:
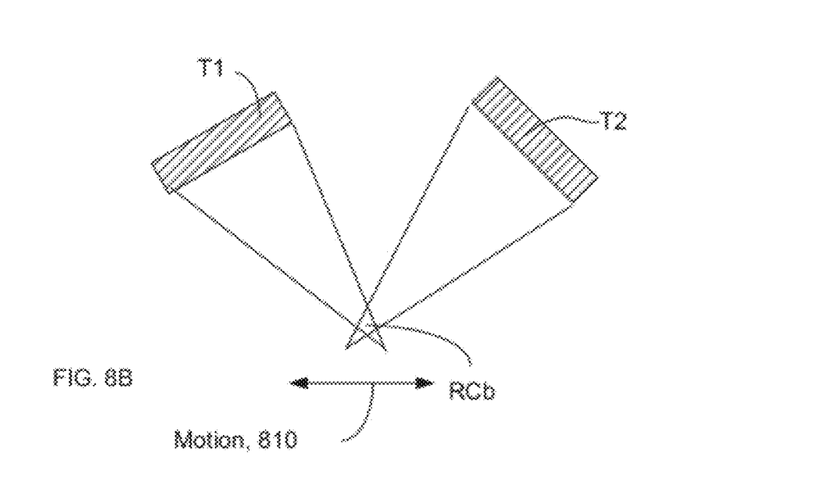
FIG. 8B is a diagram showing generalized geometry of an embodiment of the present invention having a small resolution cell.

Another advantage of the present invention is high spatial resolution. The present method facilitates measurement of the motion only in a spatial region where the primary impinging waves (beams) intersect. Focusing the impinging beams on the ROI makes is possible to define a very small spatial overlap region and, therefore, to ensure improvement in spatial resolution in comparison to conventional techniques. FIGS. 8A and 8B illustrate this advantage by showing, respectively, a configuration of a conventional CW Doppler and that of an embodiment of the present invention (VA Doppler). The beams from the conventional transmitter Tx and the receiver Rx, both of which may be transducers, overlap in a large area referred to as a resolution cell $RC_a$. The conventional system of FIG. 8A is configured to measure the velocity of particles moving in vertical direction as shown by an arrow 804 within the resolution cell $RC_a$. In contradistinction, the embodiment of VA Doppler shown in FIG. 8B, utilizes the transducers $T_1$, $T_2$ that form focused beams overlapping within a small area referred to as a resolution cell $RC_b$. The embodiment of FIG. 8B is configured to measure the velocity of objects or particles that move in the horizontal direction, as shown by an arrow 810 within the resolution cell $RC_b$. Since the resolution cell $RC_b$ is much smaller than the resolution cell $RC_a$ of the conventional CW Doppler system, the embodiment of FIG. 8B ensures higher spatial resolution than the conventional CW Doppler system. The increased spatial resolution facilitates generation of a high resolution spatial map of motion (or flow) across the object based on the scanning of the object. In contradistinction, the conventional CW Doppler method such as the CW Ultrasound Doppler has very limited spatial resolution. As a result, the user measuring the motion of the liquid flow with the use of the conventional CW US Doppler method cannot effectively measure how deep in the surrounding medium such flow runs.

Yet another advantage of this invention is the ability to measure the velocity of the object directly from the low-range frequency component with the use of simplified electronic circuitry by eliminating the need for a demodulator. For example, in the case of the US Doppler embodiment of the present invention, it is possible to detect the 1 kHz Doppler shift directly by a simple microphone (or hydrophone).

Another advantage of this invention stems from the fact that its embodiments operate in a continuous or at least a quasi-continuous (relatively long-wave) regime. A long duration signal encompasses a plurality of cycles of the Doppler shifted signal. For example, the signal duration can be in the order of 1 ms to 100 msec, which is much longer that one cycle of the received signal (that may be in the order of 20 micro seconds at 50 kHz). As a result, the receiver of the signal can advantageously use the information over a long time period (for example, integrate the signal over a long time) to detect minor changes in the frequency of the received signal. The frequency integration over a long time improves the signal-to-noise ratio (SNR). On the other hand, a Pulse Doppler system uses short pulses on the order of a few microseconds and, therefore, the registered signal power is limited. The overall SNR of a system operating in a quasi-continuous regime is increased in comparison to the SNR of a Pulse Doppler system. Consequently, embodiments of the invention are able to detect velocity of objects that are either small or otherwise having weak response to the impinging waves.

While the invention is described through the above-described exemplary embodiments, it will be understood by those of ordinary skill in the art that modifications to, and variations of, the illustrated embodiments may be made without departing from the inventive concepts disclosed herein.

Figure 6A:
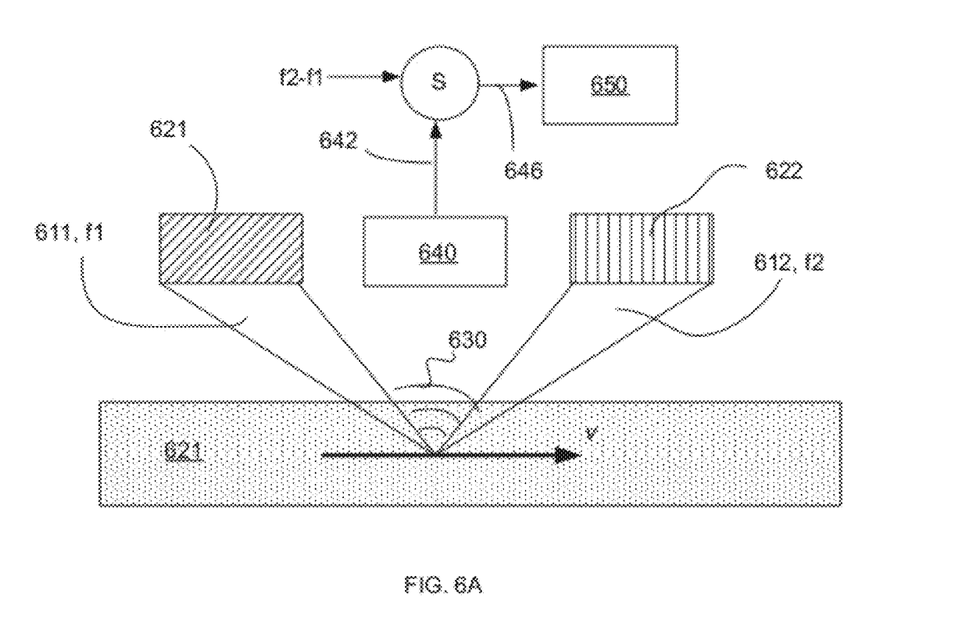
FIG. 6A is a schematic diagram showing irradiation geometry in an alternative embodiment of the invention.
Figure 6B:
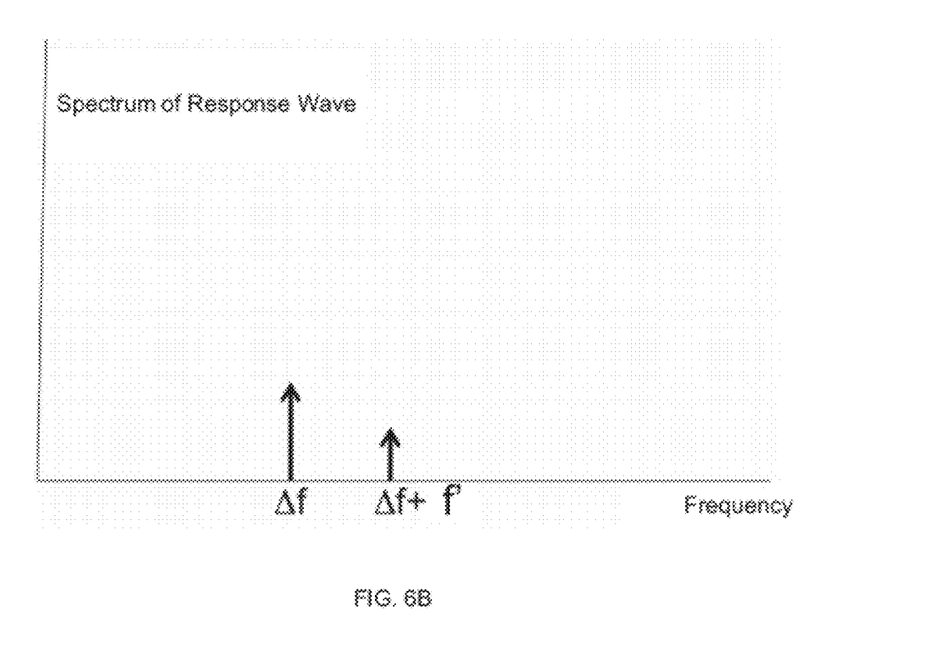
FIG. 6B is a diagraph of a frequency spectrum of a response wave generated by the embodiment of FIG. 6A.

One of such modifications, an embodiment 600 that relates to the embodiment of FIG. 2, is described in reference to FIGS. 6(A, B) and in further reference to FIG. 2. As shown, two primary US waves 611, 612 (which are respectively generated by the sources 621, 622 at respectively-corresponding US frequencies $f_1$ and $f_2 \neq f_1$ chosen such that the difference frequency, $f_A = f_1 - f_2$, is in the audible range) are focused at the ROI of the moving object 624. In this case, the response wave 630, generated by the moving object 621 in response to a non-linear interaction with the waves 611, 612 and received by a receiver 640, will have a frequency equal to $f_A + f'$ (or $f_A - f'$, depending on the direction of the flow). In a specific embodiment employing a transducer as a source of the US wave, the same transducer device may operate as a source of irradiating waves and a receiver of the response wave. FIG. 6B shows a frequency spectrum of such a response wave. The frequency component $f_A$ is still present in the spectrum as it is associated with a stationary portion of the object, while the component at $f_A + f'$ stems from the motion of the object. Generally, the "stationary" frequency component at $f_A$ can be removed by electronic means. For example, such subtraction can be implemented in a subtractor unit S, by subtracting the harmonic signal at frequency $f_A$ from the signal 642 received at the output of the receiver 640. The only frequency component $f_A + f'$ of the sound wave, remaining as a result of the subtraction, is further fed as an input 646 to a display device 250 (such as a headphone, a speaker, or a monitor) that is configured to audibly or visually present this frequency component to the user. The direction and the speed of the motion of the object can be recognized, by the user, on the basis of the pitch of sound generated by a speaker or a headphone, or by an appropriate color-coded insignia or a graphical representation such as a plot displayed on the monitor.

While a single measurement of the signal spectrum may, under some circumstances, be prone to errors, an increase of the accuracy of the measurement may be achieved, without complicating the measurement system, by performing the measurement multiple times. For example, referring again to FIGS. 2 and 7 and Eqs. (4-7), the dual measurement can be performed. In the first measurement cycle, the measurement is carried out with the source 201 is configured to transmit the wave 211 at a frequency $f_1$ and the source 202 is configured to transmit the wave 212 at a frequency $f_2$. In the second measurement cycle, however, the sources 201, 202 are re-configured transmit, respectively, the waves at $f_2$ and $f_1$. In the second measurement cycle, the Doppler frequency shift occurs in a direction opposite to that corresponding to the first measurement cycle. As a result, the spectral distribution of the resulting waves corresponding to the second measurement cycle will be symmetric to that of FIG. 4, with respect to $f_d$. The values of $f_v$, measured in such a dual-cycle, can be denoted as $f_{v+}$ and $f_{v-}$, and the accuracy of determination of the absolute value of $f_v$ by calculating an arithmetic average of the absolute values of $f_{v+}$ and $f_{v-}$ is increased.

Figure 9A:
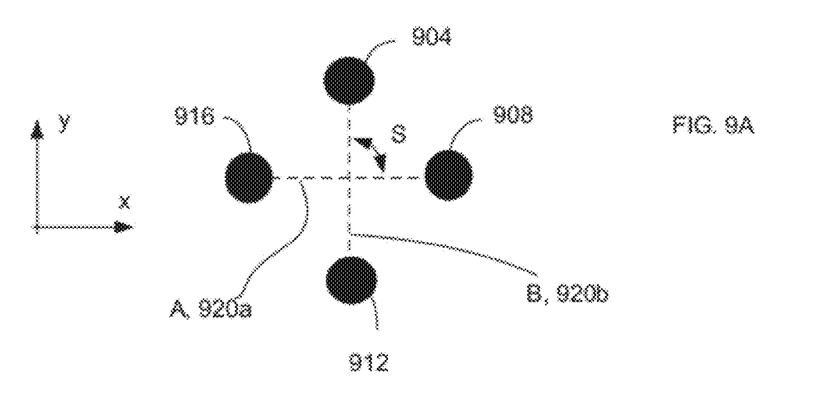
FIG. 9A is a diagram schematically showing, in top view, a Vector Doppler embodiment of the present invention.

Another modified embodiment, referred to as Vector Doppler, is shown schematically as an embodiment 900 of FIG. 9A. The embodiment 900 employs four US sources 904, 908, 912, 916 cooperated in pairs A and B (as shown by dashed lines 920a, 920b) that are disposed in a plane parallel to the xy-plane in a crossed fashion with respect to one another. The geometrical arrangement of the embodiment 900 results in a S-degree relative orientation among the pairs A, B and, as a skilled artisan will appreciate, allows for the determination of the velocity of a moving object at the ROI (not shown) in any direction in the xy-plane. As shown in the example of FIG. 9, S=90 degrees and the pairs A, B are disposed in the same plane. Generally, however, the pairs of transducers A, B can be placed in different planes that are parallel to the plane of choice (for example, the xy-plane), a relative angle at which these pairs are oriented may be different from 90 degrees, and the geometry of mutual cooperation among the transducers does not have to be symmetrical.

Figure 9B:
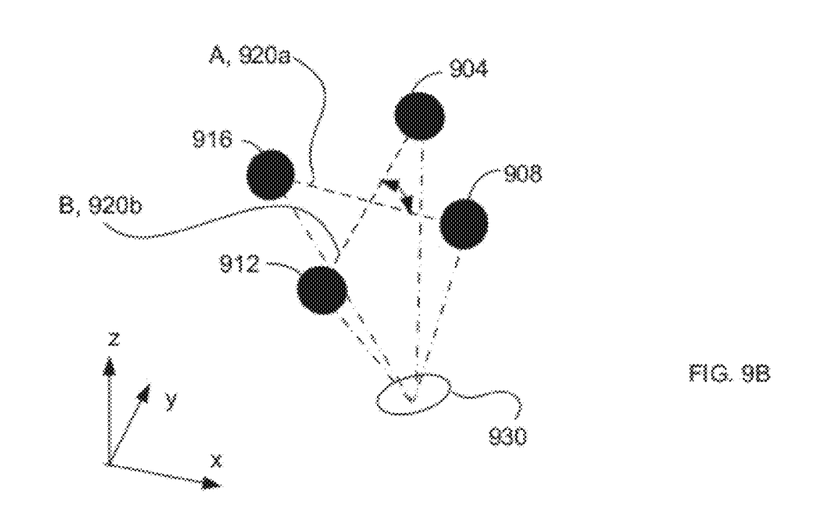
FIG. 9B is a diagram showing the embodiment of FIG. 9A in perspective view.

It is appreciated that frequencies of the US beams respectively generated by the US sources 904, 908, 912, 916 are appropriately chosen such that the difference frequencies for the transducer-pairs A, B sufficiently differ from one another. In such a case, response waves associated with pairs A, B can be measured simultaneously as these response waves do not interfere with one another. In one embodiment, for example, all four frequencies of waves generated by the sources 904, 908, 912, 916 are different. In a related embodiment, frequencies of waves generated by one pair of transducers (for example, the pair A) are substantially close to one another, while frequencies of waves generated by another pair of transducers (in this example, pair B) are different. In this case, to avoid an interference, the response waves associated with beams respectively generated by the pairs of transducers may be measured at a non-overlapping time frame. FIG. 9B is a schematic perspective view corresponding to FIG. 9A, showing the orientation of the US sources with respect to the ROI 930.

Yet another embodiment (not shown) can include—by analogy with the embodiment 900 of FIGS. 9A, 9B—three pairs of transducers respectively positioned along x, y, and z axes and operably cooperated to impinge correspondingly generated US waves onto the same ROI. Such embodiment is adapted to measure a velocity vector of the moving object in a 3D-space.

Additionally or alternatively, although some aspects of a method of the invention have been described with reference to a flowchart, those skilled in the art should readily appreciate that functions, operations, decisions, etc. of all or a portion of each block, or a combination of blocks, of the flowchart may be combined, separated into separate operations or performed in other orders. In addition, although a particular ultrasound-related embodiment of the invention and a method of detecting of the object's motion and characterizing the object's velocity have been described, the disclosed method and structure may be appropriately modified to address detection of electromagnetic waves (such as those in an optical, microwave, or a radio-frequency portion of the spectrum) without departure from the scope of the invention. Similarly one may use elastic waves to perform similar functions. In a specific case where the object in motion includes magnetic particles, these particles, in response to being vibrated by the multiple-source waves, produce a time varying magnetic field. The resulting time-varying magnetic field can then be detected by a magnetic sensor such as a coil to determine a frequency of the magnetic field, which is a function of the particle velocity, and, therefore, to determine the particle velocity itself.

In addition, it will be appreciated that in embodiments employing impinging waves that are focused onto the object under test, it is possible to incrementally translate positions of the corresponding foci of the irradiating waves thereby scanning the object and producing a map of distribution of the determined dynamic characteristic of the object. For example, as a result of appropriate spatial translation of the overlapping focal regions (such as Rayleigh ranges) of the first and second waves across blood flow the spatial distribution of the velocity (and its components, speeds and directions) of the flow can be mapped, with the use of a computer program code and an appropriate graphical display, with great precision depending, in part, on the size of the corresponding focal spots. In a specific embodiment, such spatial map displayed to the user can be additionally color-coded to facilitate the visual recognition of the changes in the dynamic characteristic across the body of the object being measured. In a related embodiment, the measurement of the object can be scaled up by aligning multiple sets of sources of the waves emitted towards the object along different directions, for example around a line encircling the moving object, such that profile distributions of the measured dynamic characteristic in several cross-section planes across the object. The collection of velocity measurements along multiple directions are then used to calculate the velocity vector (magnitude and angle) at each target point. In yet another embodiment, a source of waves irradiating an object may include an array of multiple elements.

Accordingly, the invention should not be viewed as being limited to the disclosed embodiment(s).

What is claimed is:

1. A Doppler system comprising:
   first and second pairs of sources, wherein
   the first pair contains first and second sources disposed in a first plane parallel to a reference plane,
   the second pair contains third and fourth sources disposed in a second plane parallel to the reference plane,
   the first and second sources are configured to non-collinearly transmit respective first and second waves to spatially overlap said first and second waves at a region of interest (ROI) in the reference plane, said first and second waves having, respectively, first and second frequencies, the first and second frequencies being different, the third and fourth sources are configured to non-collinearly transmit respective third and fourth waves to spatially overlap said third and fourth waves at said ROI, said third and fourth waves having third and fourth frequencies, respectively, a receiver configured to detect a first response wave produced at a first difference frequency, and to produce a first output representing said first response wave, and to detect a second response wave produced at a second difference frequency, and to produce a second output representing said second response wave, wherein the first difference frequency is defined by a difference between the first and second frequencies, the second difference frequency is defined by a difference between the third and fourth frequencies, wherein the first and second response waves are produced by first and second vibro-acoustical radiation forces that are proportional, respectively, to the square of an acoustic field generated by the first and second waves at the ROI and to the square of an acoustic field generated by the third and fourth waves at the ROI;

and an electronic circuitry operably connected to the receiver and adapted to derive, from the first and second outputs output, a dynamic characteristic of a flow regardless of a direction of propagation of the flow in the reference plane;

wherein each of the first, second, third, and fourth frequencies is between 1 MHz and 10 MHz, wherein the first and second frequencies are equal to one another, the third and fourth frequencies are equal to one another, wherein the dynamic characteristic includes a velocity of said flow, and wherein the electronic circuitry is configured to be devoid of a frequency demodulator in the receiver.

2. A system according to claim 1, wherein said first and second sources are further configured to impinge said first and second waves onto the ROI at respectively-corresponding first and second angles measured with respect to the direction of said flow, said first and second angles being equal to one another, and wherein said third and fourth sources are further configured to impinge said third and fourth waves onto the ROI at respectively-corresponding third and fourth angles measured with respect to the direction of said flow.

3. A system according to claim 1, wherein first, second, third, and fourth sources are ultrasound (US) transducers and the first, second, third, and fourth waves are US waves.

4. A system according to claim 1, wherein the dynamic characteristic includes a velocity vector of said flow and wherein the first and second planes are different planes.

5. A system according to claim 1, wherein the flow includes a motion of at least one of a biological tissue, a fluid, a gas, and a solid body.

6. A system according to claim 1, further including a scanner formatted to translate a region of an overlap of the first and second waves across the object to produce, with the use of a processor operably coordinated with the scanner, a map of spatial distribution of the dynamic characteristic of the flow.

7. A system according to claim 1, wherein the dynamic characteristic includes a velocity vector of said flow and wherein the first plane is the second plane.

8. A system according to claim 1, wherein a first line and a second line are perpendicular to one another, the first line connecting the first and second sources in the first plane, the second line connecting the third and fourth sources in the second plane.

9. A system according to claim 1, further comprising a third pair of sources containing fifth and sixth sources, wherein the fifth and sixth sources disposed on an axis that is perpendicular to the reference plane, wherein the fifth and sixth sources are configured to non-collinearly transmit respective fifth and sixth waves to spatially overlap said fifth and sixth waves at said ROI, said fifth and sixth waves having, respectively, fifth and sixth frequencies, and wherein the receiver is further configured to detect a third response wave produced at a third difference frequency, and to produce a third output representing said third response wave, the third difference frequency is defined by a difference between the fifth and sixth frequencies, wherein the third response wave is produced by a third vibro-acoustical radiation force that is proportional to the square of an acoustic field generated by the fifth and sixth waves at the ROI; and wherein said electronic circuitry is further configured to derive, from the first, second, and third outputs, a dynamic characteristic of the flow occurring at the ROI, regardless of a direction of the flow out of the reference plane.

10. A system according to claim 9, wherein said electronic circuitry is configured to interchange frequencies of waves transmitted, respectively, by sources in a pair of sources from the first, second, and third pairs, to increase an accuracy of determination of said dynamic characteristic based on comparison of (i) a response wave caused by operation of sources in said pair before the interchange of said frequencies and detected with the receiver, and (ii) another response wave caused by operation of said sources in said pair after the interchange occurred and detected by the receiver.

* * * * *